United States Patent [19]

Kaltenbach

[11] Patent Number: 5,735,299
[45] Date of Patent: Apr. 7, 1998

[54] QUICK RELEASE LINE INSERTER

[76] Inventor: Frederick H. Kaltenbach, 1138 Winged Foot Cir., West, Winter Springs, Fla. 32708

[21] Appl. No.: 799,551

[22] Filed: Feb. 13, 1997

[51] Int. Cl.[6] .................................................. A61C 15/00
[52] U.S. Cl. .......................... 132/323; 132/321; 223/99; 112/224
[58] Field of Search ............................. 132/321, 323, 132/327, 328, 329; 223/99; 112/224, 225; 433/141, 3; 606/139

[56] References Cited

U.S. PATENT DOCUMENTS

| | | | |
|---|---|---|---|
| 497,362 | 7/1893 | Mason | 132/321 |
| 542,782 | 7/1895 | Simons . | |
| 577,468 | 2/1897 | Tissington . | |
| 1,073,140 | 9/1913 | Kendig | 112/224 |
| 1,450,101 | 3/1923 | Mathewson | 112/224 |
| 1,534,171 | 4/1925 | Fickes . | |
| 2,754,833 | 7/1956 | Vecchio | 132/91 |
| 3,929,144 | 12/1975 | Tarrson et al. | 132/323 |
| 4,050,470 | 9/1977 | Miller | 132/89 |
| 4,064,883 | 12/1977 | Oldham | 132/321 |
| 5,050,625 | 9/1991 | Siekmann | 132/323 |
| 5,219,284 | 6/1993 | Velvart et al. | 433/102 |
| 5,253,661 | 10/1993 | Alonzo | 132/321 |
| 5,638,841 | 6/1997 | Levine | 132/323 |

*Primary Examiner*—John J. Wilson
*Assistant Examiner*—Pedro Philogene

[57] ABSTRACT

A quick-release line inserter having an inserter shaft (1) with a line slot (2) for containing line (3) positioned on an outside perimeter of an inserter shaft that is sized and shaped for the shaft and the line to enter a space or aperture to be threaded. The shaft can have various cross-sectional configurations. The inserter shaft also can be designedly tapered or untapered and have a design curvature for particular use conditions. The shaft is held with a shaft handle (4). Use is by positioning line on the inserter shaft, inserting the inserter shaft containing the line through a space or aperture, grasping the line at an exit side of the space or aperture, removing the inserter shaft from the space or aperture, and releasing the line from the inserter shaft.

22 Claims, 3 Drawing Sheets

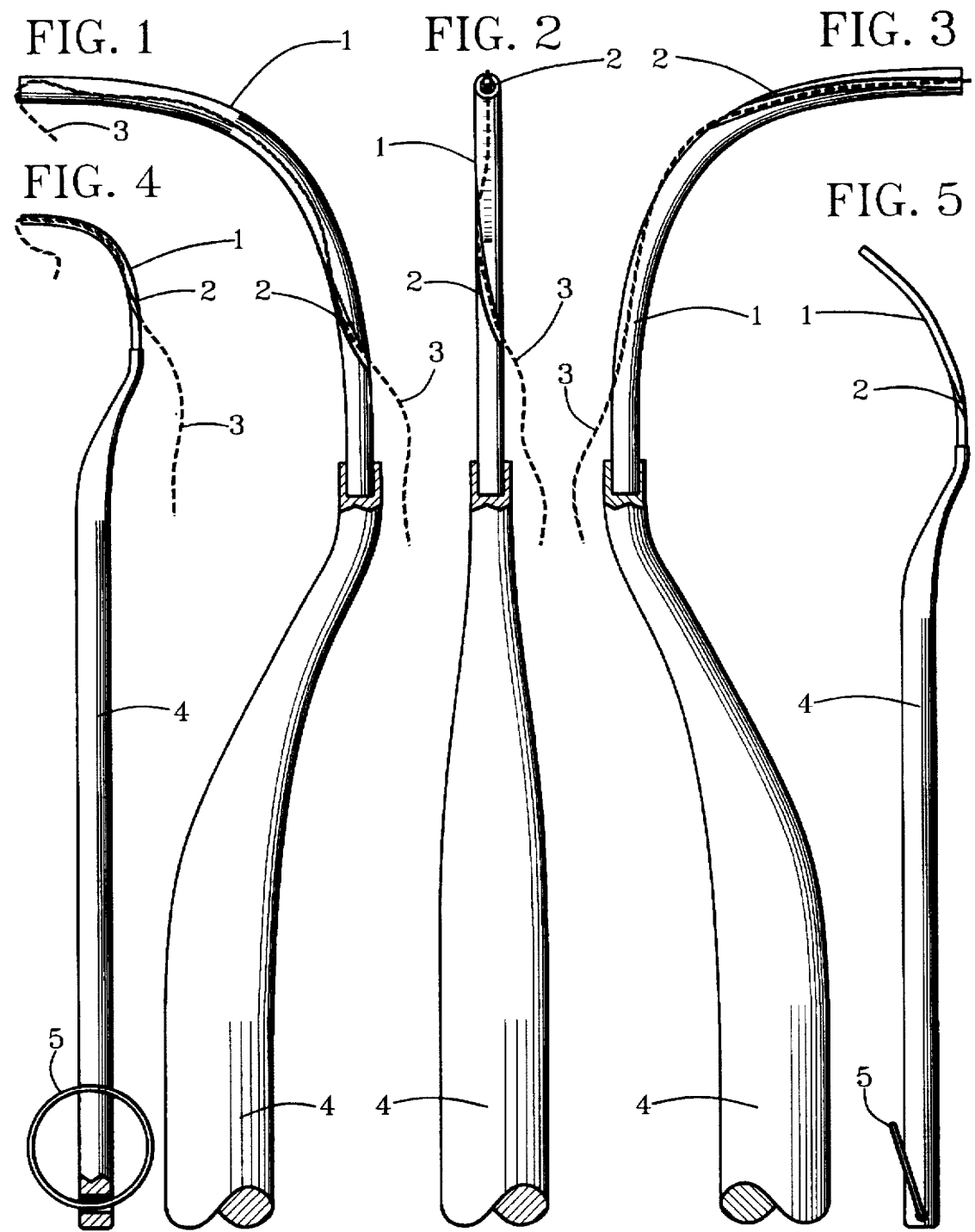

QUICK RELEASE LINE INSERTER

BACKGROUND OF THE INVENTION

This invention relates to tools for inserting lines through or into confined spaces such as inserting dental floss, dental-floss threader of other dental line between teeth and inserting thread into needle eyes and then quickly and conveniently releasing the dental floss, thread or other line from the line inserter.

Previous systems and devices for using dental floss have not been quick-release insertion tools that can be used for inserting lines such as dental floss and thread into confined spaces such as between teeth and in needle eyes and then quickly and conveniently releasing the line in a manner taught by this invention.

Different but related systems and devices are described in the following patent documents. U.S. Pat. No. 5,253,661, issued to Alonzo, taught floss-attachment means on a conical tooth pick with a cleaning scoop on a handle end. U.S. Pat. No. 5,219,284, issued to Velvart, et al., described a set of spiral tools for reaming out dental root canals. U.S. Pat. No. 5,050,625, issued to Seikmann, taught a curved floss-threading hook on a tubular handle containing a spool of dental floss. U.S. Pat. No. 4,050,470, issued to Miller, taught a pair of floss-holding handles. U.S. Pat. No. 2,754,833, taught a floss-holding extension on a back side of a toothbrush. U.S. Pat. No. 1,534,171, issued to Fickes, taught a floss-holding feature on a dental mirror. U.S. Pat. No. 557,468, issued to Tissington, taught a floss-holding wire yoke with an axial handle. U.S. Pat. No. 542,782, issued to Simons, taught a floss-holding wire yoke with a lateral handle.

SUMMARY OF THE INVENTION

In light of need for improvement of line threaders, objects of this invention are to provide a quick-release line inserter which:

Can be used for inserting dental floss between teeth and under dental bridges and then released quickly and easily;

Can be used for threading sewing-machine needles and hand-held needles;

Can be orthogonal for insertion of dental floss, lines and thread from sides; and Can be used for inserting different sizes, shapes and textures of line in a wide range of sizes, shapes and positions of apertures or spaces.

This invention accomplishes these and other objectives with a quick-release line inserter having a shaft with a slot for containing line positioned helically on an outside perimeter of a shaft that is sized and shaped for the shaft and the line to enter a space or aperture to be threaded. The shaft can have designedly tapered or untapered sides and have a design curvature for particular use conditions. The shaft is held with a handle on a base end.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF DRAWINGS

This invention is described by appended claims in relation to description of a preferred embodiment with reference to the following drawings which are described briefly as follows:

FIG. 1 is a partially cutaway and enlarged sectional view of a left side of an embodiment with a helical line slot on a cylindrical inserter shaft on a shaft end of a shaft handle;

FIG. 2 is a front view of the FIG. 1 illustration;

FIG. 3 is a right-side view of the FIG. 1 illustration;

FIG. 4 is an elevation view of the FIG. 1 illustration;

FIG. 5 is the FIG. 4 illustration with a less arcuate inserter shaft;

DESCRIPTION OF PREFERRED EMBODIMENT

Figure 6:
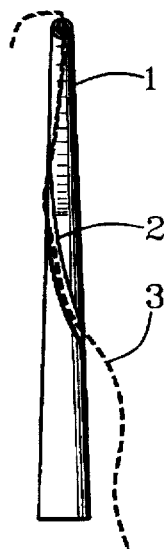
FIG. 6 is a front view of a cylindrical or truncate-conical inserter shaft having tapered sides.
Figure 7:
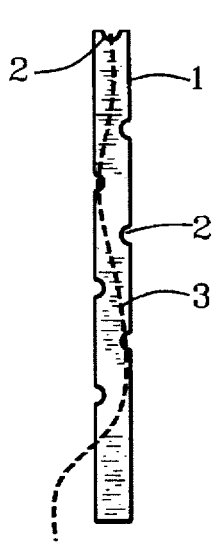
FIG. 7 is a front view of a straight inserter shaft having a rectangular cross section and a plurality of line slots staggered in edges.

For purposes of describing the preferred embodiment, the terminology used in reference to the numbered components in the drawings is as follows:

1. inserter shaft
4. shaft handle
2. line slot
5. loop handle
3. line

Reference is made first to FIGS. 1–6. An inserter shaft 1 has at least one line slot 2 positioned to contain a line 3 helically on the inserter shaft 1. The line slot 2 can be sized and shaped to receive lines 3 having a select range of cross-sectional areas for entering confined spaces having a select range of entrance sizes in association with the inserter shaft 1. A shaft handle 4 is attached to a shaft end of the inserter shaft 1.

The inserter shaft 1 can be orthogonally arcuate as depicted in FIGS. 1–4, designedly less arcuate as depicted in FIG. 5 or straight as depicted in FIGS. 7–10.

A loop handle 5 can be attached variously to an end of the shaft handle 4 for carrying and hanging the quick-release line inserter as shown in FIGS. 4–5. The loop handle 5 can be a rigid ring or a variously flexible line.

Figure 10:
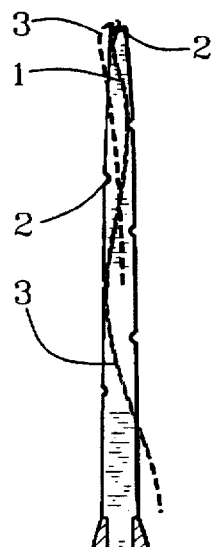
FIG. 10 is a front view of an inserter shaft having a rectangular cross section and tapered edges with relatively small line slots on edges and on an insertion end for threading needles and for entry with dental floss between closely positioned teeth.
Figure 11:
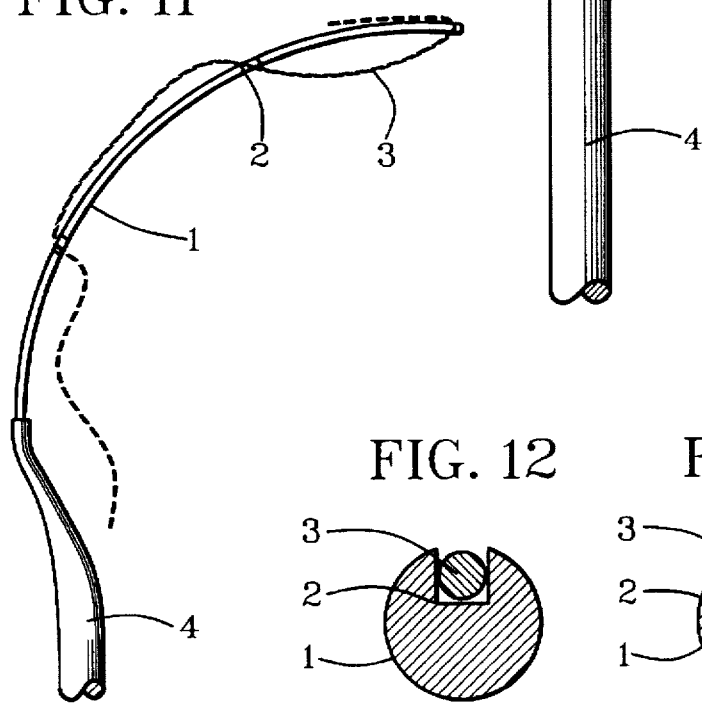
FIG. 11 is a sectional side view of an arcuate quick-release line inserter having an inserter shaft with a rectangular cross section.
Figure 12:
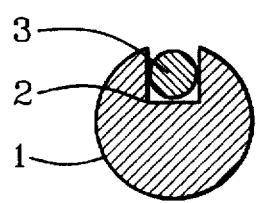
FIG. 12 is a cross sectional view of a cylindrical inserter shaft having a rectangular line slot.
Figure 13:
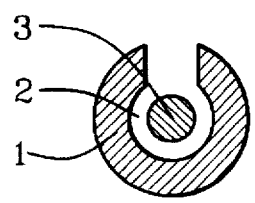
FIG. 13 is a cross sectional view of a cylindrical inserter shaft having a cylindrical line slot.
Figure 14:
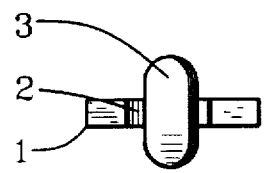
FIG. 14 is an insertion-end view of an inserter shaft with a rectangular cross section and a line positioned in a line slot in an insertion end.

Referring to FIGS. 1–14, the inserter shaft 1 can be cylindrical as depicted in FIGS. 1–6, conical or truncate-conical as depicted in FIG. 6 or plural-sided such as the rectangular configuration depicted in FIGS. 7-11 and 14. Line slots 2 can be variously cylindrical as depicted in FIGS. 2 and 13, concave as depicted in FIGS. 7-11 and 14, straight-walled as depicted in FIG. 12 or structured otherwise as appropriate for receiving and releasing particular line 3 conveniently. A relatively thin, rectangular and tapered inserter shaft 1 with a line slot 2 in an insertion end as depicted in FIG. 10 is preferable for plural-sided inserter shafts 1 to thread small needles and to insert dental floss, dental tape, floss threader or other dental line between closely positioned teeth. Corners of the rectangular inserter shaft 1 can be rounded to avoid cutting gums.

This quick-release line inserter is used by positioning a line 3 in a line slot 2, wrapping the line 3 helically on an inserter shaft 1, grasping shaft handle 4, inserting an insertion end of the inserter shaft 1 in association with the line 3 into a targeted confined area, grasping the line 3 from a side of the confined area that is opposite a side from which the inserter shaft 1 and the line 3 were inserted, removing the inserter shaft 1 from the confined area, and releasing the line 3 from the line slot 2.

For cylindrical and variously conical inserter shafts 1, one line slot 2 is provided with preferably 180 degrees of helical rotation of the line slot 2 and the line 3. For rectangular inserter shafts 1 having either parallel or tapered edges, a plurality of line slots 2 can be employed for wrapping the line 3 helically on the inserter shaft 1.

Teeth that are close together, whether under a dental bridge or separate, and small needles can be serviced particularly well with a thin and narrowly tapered rectangular inserter shaft 1 as depicted in FIG. 10. Line 3, such as dental floss or thread, can be positioned in a line slot 2 on an insertion end and held in place if desired by helically positioned line 3 with one or more helical windings in one or more line slots 2 on edges of the inserter shaft 1.

Wrapping or positioning of line 3 on the inserter shaft 1 can be relatively loose, particularly when the rectangular inserter shaft 1 is employed as depicted in FIGS. 7-11. Rectangular inserter shafts 1 can have staggered line slots 2 with either offset or in-line positioning of the line slots 2 on opposite sides.

Figure 8:
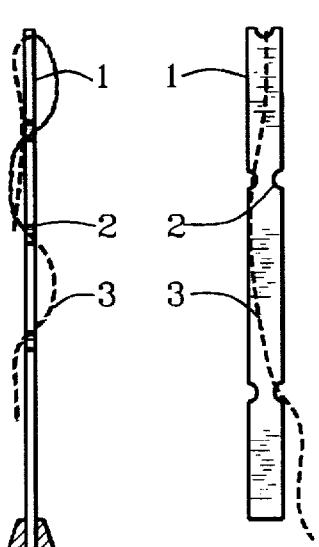
FIG. 8 is a side view of the FIG. 7 inserter shaft attached to a section of a shaft handle.
Figure 9:
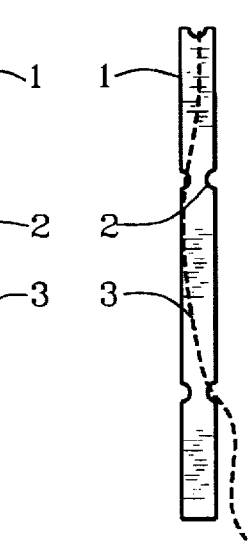
FIG. 9 is the FIG. 7 illustration with line slots oppositely disposed on sides.

FIGS. 8 and 10 illustrate a generally helical but loose wrapping of line 3 over a first section of line 3 that has been positioned in a line slot 2 at an insertion end of the inserter shaft 1. This tends to hold the line 3 in place while being inserted through a confined area with the inserter shaft 1.

Figure 15:
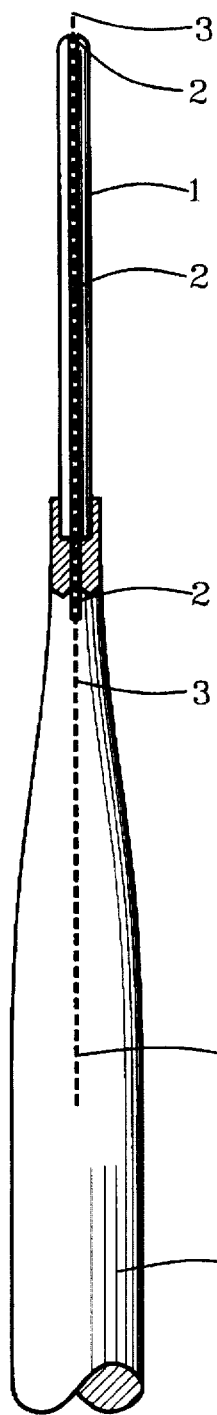
FIG. 15 is a partially cutaway sectional top view of a back of an inserter shaft having a line slot on a back side of the inserter shaft.
Figure 16:
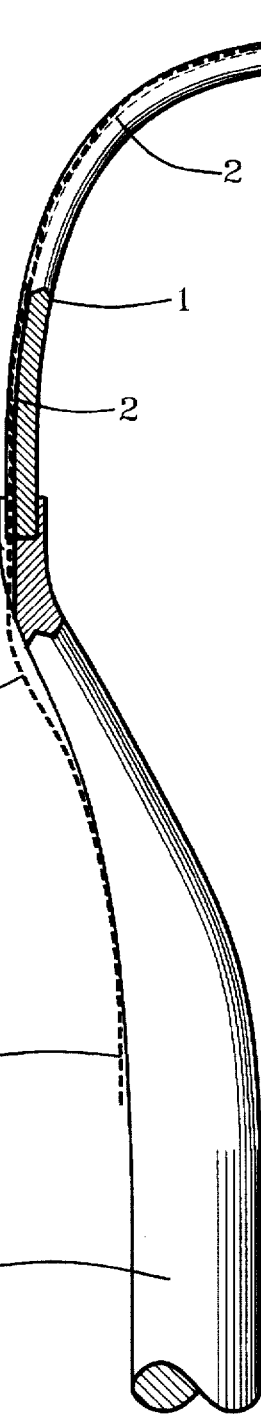
FIG. 16 is a partially cutaway side view of the FIG. 15 illustration.
Figure 17:
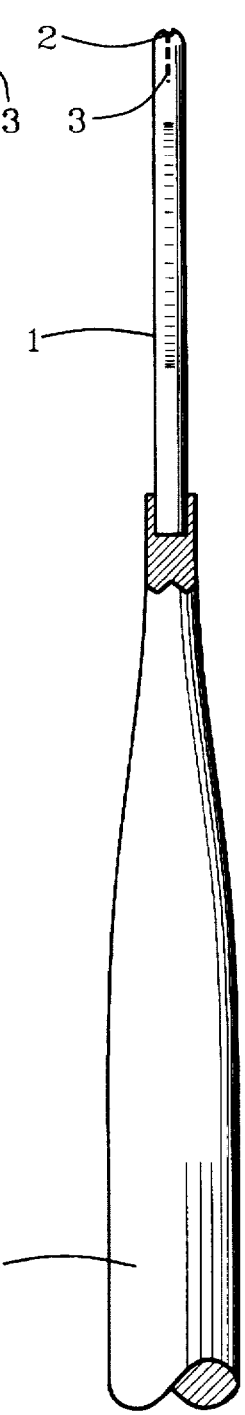
FIG. 17 is a partially cutaway front view of the FIG. 15 illustration.

Referring to FIGS. 15-17, the line slot 2 can be on a back side of the inserter shaft 1 and extend optionally into a section of the shaft handle 4 where it can be held with a finger while an end of the line 3 is looped over an insertion end of the inserter shaft 1. The line 3 is held in the line slot 2 by a finger at a handle end of the inserter shaft 2 in combination with containment by edges of an aperture or space while the inserter shaft 1 and the line 3 are being inserted through an aperture or space that is targeted.

A new and useful quick-release line inserter having been described, all such foreseeable modifications, adaptations, substitutions of equivalents, mathematical possibilities of combinations of parts, pluralities of parts, applications and forms thereof as described by the following claims and not precluded by prior art are included in this invention.

I claim:

1. A quick-release line inserter comprising:
   an inserter shaft that is sized, shaped and structured to enter confined spaces having entrances with a particular range of entrance sizes;
   at least one line slot on the inserter shaft;
   the line slot being sized, shaped and positioned to contain a line on the inserter shaft;
   the line having a design range of cross-sectional areas for entering the entrances in association with the inserter shaft;
   a shaft handle to which a handle end of the inserter shaft is attached; and
   wherein the inserter shaft is cylindrical, the line slot is positioned helically on the inserter shaft, with design degrees of helical rotation on the inserter shaft and the entrances which the inserter shaft is sized, shaped and structured to enter are spaces between teeth of an individual.

2. A quick-release line inserter as described in claim 1 wherein:
   the line having a design range of cross-sectional areas for entering the entrances in association with the inserter shaft is dental floss.

3. A quick-release line inserter as described in claim 2 wherein:
   the inserter shaft is designedly arcuate intermediate an insertion end for insertion in the confined spaces and a position of attachment of a handle end to the shaft handle.

4. A quick-release line inserter as described in claim 1 wherein:
   the entrances which the inserter shaft is sized, shaped and structured to enter are eyes of needles; and
   the line having a design range of cross-sectional areas for entering the entrances in association with the inserter shaft is sewing thread.

5. A quick-release line inserter as described in claim 1 wherein:
   the inserter shaft is tapered conically.

6. A quick-release line inserter as described in claim 5 wherein:
   the line slot is positioned helically on the inserter shaft; and
   the line slot has design degrees of helical rotation on the inserter shaft.

7. A quick-release line inserter as described in claim 6 wherein:
   the entrances which the inserter shaft is sized, shaped and structured to enter are spaces between teeth of an individual.

8. A quick-release line inserter as described in claim 7 wherein:
   the line having a design range of cross-sectional areas for entering the entrances in association with the inserter shaft is dental floss.

9. A quick-release line inserter as described in claim 7 wherein:
   the inserter shaft is designedly arcuate intermediate a distal end for insertion in the confined spaces and a position of attachment of a proximal end to the shaft handle.

10. A quick-release line inserter as described in claim 6 wherein:
    the entrances which the inserter shaft is sized, shaped and structured to enter are eyes of needles; and
    the line having a design range of cross-sectional areas for entering the entrances in association with the inserter shaft is sewing thread.

11. A quick-release line inserter as described in claim 1 wherein:
the inserter shaft is plural-sided through a cross section.

12. A quick-release line inserter as described in claim 11 wherein:
the line slot is a design plurality of slots having staggered positions on opposite sides of the inserter shaft to receive a line helically on the inserter shaft.

13. A quick release line inserter as described in claim 12 wherein:
the entrances which the inserter shaft is sized, shaped and structured to enter are spaces between teeth of an individual.

14. A quick-release line inserter as described in claim 13 wherein:
the line having a design range of cross-sectional areas for entering the entrances in association with the inserter shaft is dental floss.

15. A quick-release line inserter as described in claim 13 wherein:
the inserter shaft is designedly arcuate intermediate a distal end for insertion in the confined spaces and a position of attachment of a proximal end to the shaft handle.

16. A quick-release line inserter as described in claim 12 wherein:
the entrances which the inserter shaft is sized, shaped and structured to enter are eyes of needles; and
the line having a design range of cross-sectional areas for entering the entrances in association with the inserter shaft is sewing thread.

17. A quick-release line inserter as described in claim 12 and further comprising:
an end slot in an insertion end of the inserter shaft;
the end slot being sized and shaped to receive a portion of line to be positioned in a design plurality of slots in staggered positions on opposite sides of the inserter shaft.

18. A quick-release line inserter as described in claim 17 wherein:
at least one side of the inserter shaft on which slots are positioned is tapered from a major width at a handle end towards a minor width at an insertion end of the inserter shaft.

19. A quick-release line inserter as described in claim 12 wherein:
at least one side of the inserter shaft on which slots are positioned is tapered from a major width at a handle end towards a minor width at an insertion end of the inserter shaft.

20. A quick-release line inserter as described in claim 16 wherein:
at least one side of the inserter shaft on which slots are positioned is tapered from a major width at a handle end towards a minor width at an insertion end of the inserter shaft.

21. A quick-release line inserter as described in claim 13 wherein:
at least one side of the inserter shaft on which slots are positioned is tapered from a major width at a handle end towards a minor width at an insertion end of the inserter shaft.

22. A quick-release line inserter as described in claim 1 wherein:
the line slot is on an outside of an arcuate inserter shaft, such that line in the line slot can be held with a finger proximate a handle end of the inserter shaft and a distal end of the line is looped over an insertion end of the inserter shaft.

* * * * *